(12) United States Patent
Furukawa et al.

(10) Patent No.: US 6,743,803 B2
(45) Date of Patent: Jun. 1, 2004

(54) MEDICINES FOR THE PREVENTION AND TREATMENT OF NEURODEGENERATIVE DISEASES

(75) Inventors: Kiyoshi Furukawa, Shiga-gun (JP); Satoshi Kurumiya, Nishinomiya (JP); Kazuo Okimoto, Osaka (JP); Kazunori Ohno, Ikoma (JP)

(73) Assignee: Dainippon Pharmaceutical Co., Ltd., Osaka-Fu (JP)

( * ) Notice: Subject to any disclaimer, the term of this patent is extended or adjusted under 35 U.S.C. 154(b) by 0 days.

(21) Appl. No.: 10/311,932

(22) PCT Filed: Jun. 12, 2001

(86) PCT No.: PCT/JP01/04934
§ 371 (c)(1),
(2), (4) Date: Dec. 20, 2002

(87) PCT Pub. No.: WO01/98300
PCT Pub. Date: Dec. 27, 2001

(65) Prior Publication Data

US 2003/0166673 A1 Sep. 4, 2003

(30) Foreign Application Priority Data

Jun. 21, 2000 (JP) .................................. 2000-185814

(51) Int. Cl.[7] .................... A61K 31/4375; C07D 471/04
(52) U.S. Cl. ............................... 514/300; 546/122
(58) Field of Search ............................ 514/300, 299; 546/122

(56) References Cited

U.S. PATENT DOCUMENTS 6,172,079 B1 * 1/2001 Ohno et al. .................. 514/300

FOREIGN PATENT DOCUMENTS

| JP | 5-221997 | 8/1993 |
| JP | 9-291034 | 11/1997 |
| WO | 99/03857 | 1/1999 |
| WO | 00/73283 | 12/2000 |

OTHER PUBLICATIONS

Elliot D. Luby, M.D., et al., "Study of a New Schizophrenomimetic Drug–Sernyl", Archives of Neurology and Psychiatry, vol. 81, pp. 363–369, 1959.

Gaylord Ellison, "The N–methyl–D–aspartate antagonists phencyclidine, ketamine and dizocilpine as both behavioral and anatomical models of the dementias", Brain Research Reviews, 20, pp. 250–267, 1995.

D.F. Wozniak et al., "MK–801 neurotoxicity in male mice: histologic effects and chronic impairment in spatial learning" 707, pp. 165–179, 1996.

John W. Olney et al., "NMDA receptor hyopfunction model of schizophrenia", Journal of Psychiatric Research, 33, pp. 523–533, 1999.

Pete Andine, et al., "Characterization of MK–801–Induced Behavior as a Putative Rat Model of Psychosis", Journal of Pharmacol. Experimental Therapeutics, vol. 290, pp. 1393–1408, 1999.

J.W. Olney, et al., "NMDA Antagonist Neurotoxicity: Mechanism and Prevention", Science, vol. 254, pp. 1515–1518, 1991.

* cited by examiner

*Primary Examiner*—Charanjit S. Aulakh
(74) *Attorney, Agent, or Firm*—Wenderoth, Lind & Ponack, L.L.P.

(57) ABSTRACT

Medicines for the prevention and treatment of neurodegenerative diseases such as Alzheimer's disease and schizophrenia of mammals (including human beings) through the retardation or inhibition of neurodegeneration due to hypofunction of glutamic acid receptor and which contain as an active ingredient 5-substituted-3-oxadiazolyl-1,6-naphthyridin-2(1H)-one derivatives of the formula (I):

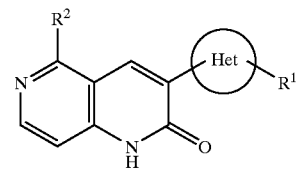

wherein Het is oxadiazolyl; $R^1$ is hydrogen, lower alkyl, cyclo-lower alkyl, lower alkenyl, lower alkoxy, substituted or unsubstituted aryl, substituted or unsubstituted heteroaryl, etc.; and $R^2$ is hydrogen, lower alkyl, cyclo-lower alkyl, substituted or unsubstituted aryl, etc., or physiologically acceptable acid addition salts thereof.

10 Claims, No Drawings

MEDICINES FOR THE PREVENTION AND TREATMENT OF NEURODEGENERATIVE DISEASES

TECHNICAL FIELD

The present invention relates to a medicine for the prevention and treatment of neurodegenerative diseases comprising a 5-substituted-3-oxadiazolyl-1,6-naphthyridin-2 (1H)-one derivative or a physiologically acceptable acid addition salt thereof as an active ingredient, and use of said compound for the manufacture of a medicine for the prevention and treatment of neurodegenerative diseases.

BACKGROUND ART

With developing into an aging society, the number of patients suffering from neurodegenerative diseases such as Alzheimer's disease is increasing. Alzheimer's disease is a progressive neurodegenerative disorder of the central nervous system which symptoms are mainly attenuation and decline of memory, and it is suggested by the neurochemical studies that the main cause is dysfunction of neurotransmissions in plural neurotransmitter systems such as acetylcholine, γ-aminobutyric acid (GABA), glutamic acid, and dopamine. On the basis of the finding that the neuronal dysfunction occurs remarkably in cholinergic system among those systems, a medicine has been developed for the purpose of improvement in cognitive deficits by means of the activation of cholinergic system.

Besides, there are also some attempts to develop benzodiazepine (BZP) receptor inverse agonists as the therapeutic agent for treatment of dementia. Heretofore, many studies have been done on the relationship between the binding-manner to the BZP receptor and the pharmacological activity, and in view of the pharmacological activity thereof, BZP agonists have been used as antianxiety drugs (e.g. diazepam), as hypnotics (e.g. triazolam), or as antiepileptic drugs (e.g. clonazepam). However, it is well-known that administration of BZP agonists causes amnesia (amnesic action) as a side effect. On the other hand, since it is known that BZP inverse agonists exhibit the actions opposite to those of BZP agonists, and enhance cholinergic activity which is considerably related with cognitive function, the inverse agonist is expected to have the anti-dysmnesia action (anti-amnesia action) and to activate cerebral function.

As an example of such a compound, WO 99/03857 discloses 5-substituted-3-oxadiazolyl-1,6-naphthyridin-2 (1H)-one derivatives of the following formula:

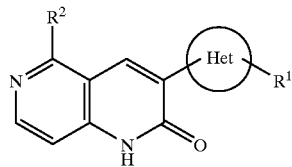

wherein Het is an oxadiazolyl group;

R$^1$ is a hydrogen, a lower alkyl group, a cyclo-lower alkyl group, a lower alkenyl group, a lower alkoxy group, a substituted or unsubstituted aryl group, a substituted or unsubstituted heteroaryl group, etc.; and R$^2$ is a hydrogen, a lower alkyl group, a cyclo-lower alkyl group, a substituted or unsubstituted aryl group, etc., in which it is described that said compounds exhibit selective and high affinity to benzodiazepine receptor and are useful as benzodiazepine receptor ligands, especially as inverse agonists, which are expected to be cerebral activators or therapeutic agents for treatment of senile dementia and Alzheimer's disease.

Recently, it has been indicated that schizophrenia and Alzheimer's disease are related with the hypofunction of ion-channel type N-methyl-D-aspartic acid (hereinafter, abbreviated to "NMDA") receptor, which is a subtype of glutamic acid receptors. Phencyclidine, a noncompetitive antagonist of NMDA receptor, exhibits excellent pharmacological activities such as anesthetic activity and neuroprotective activity for acute encephalopathy, while it has been ever used for the undesirable purpose of extensive drug abuse as street drug. After E. D. Luby et al. reported that phencyclidine caused schizophrenia-like hallucination and mental aberration in human beings [Archives Neurology and Psychiatry. Vol 81, pp 363–369 (1959)], a lot of studies thereof have been accumulated until today. It has been proved that phencyclidine causes schizophrenia-like hallucination and mental aberration in human beings more strongly than amphetamine or LSD (9,10-didehydro-N,N-diethyl-6-methyl-ergoline-8β-carboxamide). Additionally, in the case of animals, it is known that NMDA receptor antagonists such as phencyclidine, MK-801 (dizocilpine maleate: (+)-10,11-dihydro-5-methyl-5H-dibenzo[a,d] cyclohepten-5,10-imine maleate) and ketamine, cause the enhancement of spontaneous motor activity and aberrant behaviors related with the symptoms of mental aberration such as hallucination, as well as ataxia, and such behavioral changes are suppressed by medicines for schizophrenia (e.g. haloperidol, risperidone and olanzapine), antianxiety drugs (e.g. diazepam), and antagonists of NMDA receptor glycine site (e.g. HA-966: R(+)-3-amino-1-hydroxy-2-pyrrolidinone). It is also known that NMDA receptor antagonists (MK-801, phencyclidine and ketamine) cause learning/memory disorder in animals. Consequently, a medicine suppressing hypofunction of NMDA receptor is expected to be useful for therapy of dysmnesia and schizophrenia.

It is known that MK-801 is a noncompetitive antagonist for NMDA receptor, which is a subtype of glutamate receptors, and encephalic neuronopathy (leading to cell death via cell vacuolization) is caused by the systemic administration of said agent to animals. That is, in the case of the single application of MK-801 at moderate doses (0.3–1.0 mg/kg), neuronal vacuolization is observed in the posterior cingulate (PC)/retrosplenial cortex (RS) (hereinafter, abbreviated to PC/RS cortex) in 4–5 hours after administration, and in the case of higher doses (3–10 mg/kg), necrosis of neurons and hyperplasia of glial cells are observed in a few days to a few weeks after administration. Besides, in the case of repeated application, the damage spreads to hippocampal ventral dentate gyrus and limbic regions such as entorhinal cortex and amygdala. It is presumed that the hypofunction of NMDA receptor may cause neurodegeneration in the PC/RS cortex through complicated polysynaptic network mechanism [in which at least 7 receptors, i.e. glutamic acid (NMDA and non-NMDA), acetylcholine-M3, adrenaline-α2, GABA-A, sigma and serotonin 2A, are involved], since such neurodegeneration would be caused by both noncompetitive antagonists of NMDA receptor (phencyclidine and ketamine) and competitive antagonists [e.g. D-2-amino-5-phosphono-pentanoic acid (D-AP5)]. It is considered that the dysfunction of NMDA receptor caused by administration of MK-801 may be closely related to the onset of neurodegenerative diseases, and hence the neuronopathy induced by MK-801 will be usable as a pathological model of neurodegenerative diseases [see, G. Ellison. Brain Research Reviews. Vol 20, pp 250–267 (1995); D. F. Wozniak et al., Brain Research. Vol 707, pp 165–179 (1996); J. W. Olney et al., J. Psychiatric Research. Vol 33, pp 523–533 (1999); P. Andine et al., J. Pharmacol. Exp. Ther., Vol 290, pp 1393–1408 (1999)].

It is known that medicines inhibiting MK-801-induced neuronopathy include anticholinergic drugs (e.g. scopolamine and atropine), barbiturate hypnotics (e.g. pentobarbital and thiopental), and benzodiazepine derivatives (e.g. diazepam) [see, J. W. Olney et al., Science, Vol 254, pp 1515–1518 (1991)].

The present inventors have found that 5-substituted-3-oxadiazolyl-1,6-naphthyridin-2(1H)-one derivatives of the formula (I) or physiologically acceptable acid addition salts thereof exhibit an extremely potent inhibitory effect on the MK-801-induced neurodegeneration in the PC/RS cortex by using the above pathological model.

DISCLOSURE OF INVENTION

An object of the present invention is to provide a medicine for the prevention and treatment of neurodegenerative diseases comprising a 5-substituted-3-oxadiazolyl-1,6-naphthyridin-2(1H)-one derivative of the following formula (I):

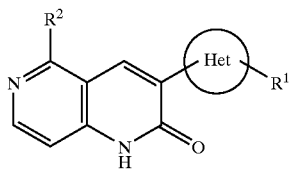

wherein:
Het is an oxadiazolyl group;
$R^1$ is a hydrogen atom, a lower alkyl group, a cyclo-lower alkyl group, a trifluoromethyl group, a lower alkenyl group, a lower alkynyl group, a lower alkoxy group, a lower alkoxy-lower alkyl group, a hydroxy-lower alkyl group, a substituted or unsubstituted aryl group, or a substituted or unsubstituted heteroaryl group; and
$R^2$ is a hydrogen atom, a lower alkyl group, a cyclo-lower alkyl group, a cyclo-lower alkylmethyl group, a lower alkenyl group, a cyclo-lower alkenyl group, a lower alkynyl group, a substituted or unsubstituted aryl group, or a substituted or unsubstituted heteroaryl group, or a physiologically acceptable acid addition salt thereof.

Another object of the present invention is to provide use of a 5-substituted-3-oxadiazolyl-1,6-naphthyridin-2(1H)-one derivative of the formula (I) or a physiologically acceptable acid addition salt thereof for the manufacture of a medicine for the prevention and treatment of neurodegenerative diseases.

A further object of the present invention is to provide a method for the prevention and/or treatment of neurodegenerative diseases in mammals (including human beings), which comprises administering an effective amount of a 5-substituted-3-oxadiazolyl-1,6-naphthyridin-2(1H)-one derivative of the formula (I) or a physiologically acceptable acid addition salt thereof to said mammals in need of such prevention and/or treatment.

BEST MODE FOR CARRYING OUT THE INVENTION

The present inventors have found that the 5-substituted-3-oxadiazolyl-1,6-naphthyridin-2(1H)-one derivative of the above formula (I) can be used for the prevention and/or treatment of neurodegenerative diseases with hypofunction of glutamic acid receptor, such as Alzheimer's disease or schizophrenia, in mammals (including human beings).

The compounds used for the prevention and treatment of neurodegenerative diseases of the present invention are shown by the formula (I), and the preferred compounds are those of the formula (I) wherein $R^1$ is a $C_1$–$C_3$ alkyl group, a $C_3$–$C_4$ cycloalkyl group, or a $C_2$–$C_3$ alkenyl group; and $R^2$ is a hydrogen atom, a $C_1$–$C_4$ alkyl group, a $C_3$–$C_6$ cycloalkyl group, a substituted or unsubstituted aryl group, or a substituted or unsubstituted heteroaryl group.

More preferred compounds are those of the formula (I) wherein $R^1$ is a $C_1$–$C_3$ alkyl group or a $C_3$–$C_4$ cycloalkyl; and $R^2$ is a hydrogen atom, a $C_1$–$C_3$ alkyl group, a $C_3$–$C_4$ cycloalkyl group, a substituted or unsubstituted phenyl group, or a substituted or unsubstituted heteroaryl group.

Further more preferred compounds are the following compounds;
3-(5-ethyl-1,2,4-oxadiazol-3-yl)-5-(2-methylcyclopropyl)-1,6-naphthyridin-2(1H)-one,
3-(5-methyl-1,2,4-oxadiazol-3-yl)-5-(2-methylphenyl)-1,6-naphthyridin-2(1H)-one,
3-(5-methyl-1,2,4-oxadiazol-3-yl)-5-(3-methoxyphenyl)-1,6-naphthyridin-2(1H)-one,
3-(5-methyl-1,2,4-oxadiazol-3-yl)-5-(4-methoxyphenyl)-1,6-naphthyridin-2(1H)-one,
3-(5-ethyl-1,2,4-oxadiazol-3-yl)-5-(2-thienyl)-1,6-naphthyridin-2(1H)-one,
3-(5-methyl-1,2,4-oxadiazol-3-yl)-5-(4-pyridyl)-1,6-naphthyridin-2(1H)-one,
3-(3-ethyl-1,2,4-oxadiazol-5-yl)-5-methyl-1,6-naphthyridin-2(1H)-one,
3-(3-ethyl-1,2,4-oxadiazol-5-yl)-5-(3-fluorophenyl)-1,6-naphthyridin-2(1H)-one,
3-(3-methyl-1,2,4-oxadiazol-5-yl)-5-(3-methylphenyl)-1,6-naphthyridin-2(1H)-one,
3-(3-methyl-1,2,4-oxadiazol-5-yl)-5-(3-methoxyphenyl)-1,6-naphthyridin-2(1H)-one,
3-(3-ethyl-1,2,4-oxadiazol-5-yl)-5-(4-methoxyphenyl)-1,6-naphthyridin-2(1H)-one,
3-(3-ethyl-1,2,4-oxadiazol-5-yl)-5-(4-pyridyl)-1,6-naphthyridin-2(1H)-one, and
3-(3-cyclopropyl-1,2,4-oxadiazol-5-yl)-5-(3-thienyl)-1,6-naphthyridin-2(1H)-one.

Suitable examples of physiologically acceptable acid addition salts of the compounds of the formula (I) are inorganic acid salts such as hydrochloride, hydrobromide, hydroiodide, sulfate, or phosphate, and organic acid salts such as oxalate, maleate, fumarate, malonate, lactate, malate, citrate, tartrate, benzoate, methanesulfonate, or tosylate.

The "lower alkyl group" and "lower alkyl" moiety in the present description denote a straight chain or branched chain alkyl group having 1–6 carbon atoms, such as methyl group, ethyl group, propyl group, isopropyl group, butyl group, isobutyl group, tert-butyl group, pentyl group, and hexyl group.

The "cyclo-lower alkyl group" denotes a cycloalkyl group having 3–6 carbon atoms, such as cyclopropyl group, cyclobutyl group, cyclopentyl group, and cyclohexyl group, and these rings may be optionally substituted by a $C_1$–$C_3$ alkyl group or a halogen atom.

The "lower alkenyl group" and "lower alkynyl group" have a straight or branched carbon chain having 2–6 carbon atoms, and include, for example, allyl group, 1-propenyl group, propargyl group, and 2-methyl-1-ethynyl group.

The "cyclo-lower alkenyl group" denotes a cycloalkenyl group having 5–6 carbon atoms, such as cyclohexenyl group.

The "lower alkoxy group" and "lower alkoxy" moiety denote a straight chain or branched chain alkoxy group having 1–6 carbon atoms, such as methoxy group, ethoxy group, propoxy group, isopropyloxy group, butyloxy group, isobutyloxy group, tert-butyloxy group, pentyloxy group, and hexyl group.

The "aryl group" and "aryl" moiety denote a phenyl group or a naphthyl group, and said ring may optionally have 1–3 substituents selected from a halogen atom, a $C_1$–$C_3$ alkyl group, a trifluoromethyl group, a hydroxy group, a $C_1$–$C_3$ alkoxy group, a trifluoromethoxy group, a cyano group, an amino group, and a nitro group.

The "heteroaryl group" denotes a 5- to 6-membered aromatic heterocyclic group containing 1–2 hetero atoms, which are, the same or different, selected from nitrogen atom, oxygen atom or sulfur atom, and includes, for example, furyl, thienyl, pyrrolyl, oxazolyl, isoxazolyl, pyridyl, pyridazinyl, and pyrimidinyl, wherein such heterocyclic group may optionally have 1 to 3 substituents selected from a halogen atom, a $C_1$–$C_3$ alkyl group, a hydroxy group, a $C_1$–$C_3$ alkoxy group, and an amino group.

Further, the "halogen atom" denotes fluorine atom, chlorine atom, bromine atom or iodine atom.

The compounds of the formula (I) can be prepared by the method disclosed in WO99/03857.

Pharmacological Experiments

The utility of the compounds of the formula (I) as the medicine for prevention and treatment of neurodegenerative diseases will be illustrated by the following pharmacological tests using a model for MK-801-induced neuronopathy and the results thereof as to the typical compounds of the formula (I).

3-(5-Methyl-1,2,4-oxadiazol-3-yl)-5-(3-methoxyphenyl)-1,6-naphthyridin-2(1H)-one (hereinafter, referred to as "Compound A") was used as a test compound. Compound A can be prepared according to the method disclosed in PCT Publication WO 99/03857.

Further, MK-801 (dizocilpine maleate) is described in, for example, Merck Index, 12th Edition, 3451 (1996), and is commercially available, (for example, (+)MK-801, manufactured by Research Biochemical International)

Experiment 1
Inhibitory Effect on MK-801-Induced Neurodegeneration

The pharmacological test was carried out according to the method of D. F. Wozniak, et al. [Brain Research, Vol. 707, pp 165–178 (1996)].

MK-801 was dissolved in physiological saline (concentration 0.1 mg/ml) and was subcutaneously (s.c.) administered to three mice (Std-ddY male mice: 39.9–45.8 g of body weight) in a volume of 0.1 ml per 10 g of body weight, i.e., 1 mg/kg. Compound A was suspended in a 0.5% tragacanth solution in a concentration of 0.1 mg/ml, and the resultant suspension was orally (p.o.) administered to the mice in a volume of 0.1 ml per 10 g of body weight, i.e., 1 mg/kg, 30 minutes before MK-801 administration. Five hours after MK-801 administration, mice were perfused with physiological saline and fixed with 10% neutral formalin buffer solution under etherization. The cerebrum was cut transversely from the anterior termination at approximately 4 mm to the posterior termination, and then embedded in cold polymerized resin (Technovit7100, manufactured by Kulzer in Germany). The slices containing the PC/RS cortex were obtained at four Anterior-Posterior levels at intervals of 300 μm from the exposed section of the block, and at each level two slices (3 μm in thickness) were consecutively obtained. The histological change (on Hematoxylin and eosin stain specimen) and the number of vacuolized neurons (on Nissl stain specimen) were observed by a light microscope for each 4 slices, respectively. The results are shown in Table 1.

Table 1 shows the number of vacuolized neurons in the PC/RS cortex in the non-treated control group, the group treated with MK-801 alone, and the group treated with Compound A before MK-801.

As shown in Table 1, in the group treated with MK-801 (1 mg/kg) for 5 hours, the vacuolization was remarkably observed in the neurons of layers III–IV, and the mean number of the vacuolized neurons per mouse remarkably increased from 0 (in non-treated control group) to 30.8 per slice. On the contrary, in the group treated with Compound A (1 mg/kg) prior to MK-801, the number remarkably decreased to 4.3, and in some of them no vacuolization was observed.

TABLE 1

| Test Group | Animal No. | Slice No. 1 | 2 | 3 | 4 | Mean(/slice) Individual | Group |
|---|---|---|---|---|---|---|---|
| Non-treatment control group | 01M01 | 0 | 0 | 0 | 0 | 0.0 | 0.0 |
|  | 01M02 | 0 | 0 | 0 | 0 | 0.0 |  |
|  | 01M03 | 0 | 0 | 0 | 0 | 0.0 |  |
| MK-801 1 mg/kg s.c. 5 h group | 02M01 | 41 | 50 | 34 | 19 | 36.0 | 30.8 |
|  | 02M02 | 23 | 39 | 42 | 40 | 36.0 |  |
|  | 02M03 | 26 | 24 | 14 | 17 | 20.3 |  |
| Compound A 1 mg/kg p.o. + MK-801 1 mg/kg s.c. 5 h group | 03M01 | 0 | 0 | 0 | 0 | 0.0 | 4.3 |
|  | 03M02 | 20 | 12 | 10 | 5 | 11.8 |  |
|  | 03M03 | 0 | 0 | 2 | 2 | 1.0 |  |

As is clear from the above results, Compound A exhibited a potent retardation or inhibition of neurodegeneration in the PC/RS cortex induced by MK-801. Accordingly, the compounds (I) of the present invention are useful for the treatment of Alzheimer's disease or schizophrenia, as a medicine for the prevention and treatment of neurodegenerative diseases on the basis of inhibitory effect on neurodegeneration, through the different mechanism from that of the current medicines for the improvement in neural hypofunction via the activation of cholinergic function.

Usage of Compounds of the Invention as Medicine

The compounds of the formula (I) can be used as a medicine for the prevention and treatment of neurodegenerative diseases. They can be administered through any of oral, parenteral and intrarectal routes, preferably oral route. The dosage thereof may vary depending on the administration route, kinds of diseases to be treated, symptom/age of patients, deal mode (prevention or treatment), etc., but it is usually in 0.01 to 10 mg/kg/day, preferably 0.02 to 5 mg/kg/day, which may be administered at one time or dividedly in several times.

The compounds of the formula (I) can be used as a medicine for the prevention and treatment of neurodegenerative diseases alone or in the form of a pharmaceutical composition, which is generally prepared by mixing with a pharmaceutically acceptable carrier. The pharmaceutical composition may be in the dosage forms such as tablets, capsules, granules, powders, syrups, suspensions, suppositories, gels, sustained release preparations, and injection preparations. These pharmaceutical compositions can be prepared by a conventional method. The pharmaceutically acceptable carrier may be any conventional ones, which are commonly used in the pharmaceutical field and do not react with the compounds of the present invention. Suitable examples are lactose, glucose, mannitol, dextrin, starch, corn starch, sucrose, polysaccharide, magnesium aluminometasilicate, synthetic aluminum silicate, crystalline cellulose, sodium carboxymethylcellulose, calcium carboxymethylcellulose, hydroxypropyl starch, ion exchange resins, methylcellulose, gelatin, acacia, hydroxypropylcellulose, low-substituted hydroxypropylcellulose, hydroxypropylmethylcellulose, poly-vinylpyrrolidone, polyvinyl alcohol, light anhydrous silicic acid, magnesium stearate, talc, carboxyvinyl polymer, titanium oxide, sorbitan fatty acid ester, sodium lauryl sulfate, glycerin, glycerin fatty acid ester, purified lanolin, glycerogelatin, polysorbate, macrogol, vegetable oil, wax, liquid paraffin, white petrolatum, nonionic surfactant, propylene glycol, and water.

Liquid preparations may be in the form, which is dissolved or suspended in water or other appropriate medium when used. Further, tablets and granules may be coated in a conventional manner. In the case of suppositories, the base for them includes cacao butter, glycerin saturated fatty acid ester, glycerogelatin, macrogol, etc., and in the preparations, a surfactant or a preservative may optionally be added. Injection preparations may be prepared by dissolving a physiologically acceptable acid addition salt of the compound of the formula (I) in distilled water for injection or physiological saline, and thereto may be optionally added a solubilizer, an isotonic agent, a pH adjusting agent, a buffering agent, a pain-reducing agent or a preservative.

These pharmaceutical compositions may usually contain the compound of the formula (I) as an active ingredient in an amount of at least 0.01% by weight, preferably 0.05–70% by weight. These pharmaceutical compositions may optionally contain other therapeutically effective compounds.

Preparation

The pharmaceutical compositions of the medicine for the prevention and treatment of neurodegenerative diseases according to the present invention are illustrated by the following preparations.

| Preparation 1: Capsules: | |
|---|---|
| 3-(5-Methyl-1,2,4-oxadiazol-3-yl)-5-(3-methoxyphenyl)-1,6-naphthyridin-2(1H)-one | 5 g |
| Corn starch | 57 g |
| Lactose | 10 g |
| Crystalline cellulose | 25 g |
| Hydroxypropylcellulose | 2 g |
| Light anhydrous silicic acid | 0.5 g |
| Magnesium stearate | 0.5 g |

Amongst the above components, the active ingredient, corn starch, lactose and crystalline cellulose are blended, and thereto is added hydroxypropylcellulose being dissolved in water, and the mixture is kneaded, dried and granulated. To these granules are added magnesium stearate and light anhydrous silicic acid and mixed. These are filled in 1000 capsules to prepare the capsule preparations weighing 100 mg each.

| Preparation 2: Tablets: | |
|---|---|
| 3-(5-Methyl-1,2,4-oxadiazol-3-yl)-5-(3-methoxyphenyl)-1,6-naphthyridin-2(1H)-one | 5 g |
| Corn starch | 20 g |
| Lactose | 19 g |
| Crystalline cellulose | 10 g |
| Hydroxypropylcellulose | 5 g |
| Low-substituted hydroxypropylcellulose | 10 g |
| Magnesium stearate | 0.5 g |
| Light anhydrous silicic acid | 0.5 g |

Amongst the above components, the active ingredient, corn starch, lactose, low-substituted hydroxypropylcellulose and crystalline cellulose are blended, and thereto is added hydroxypropylcellulose being dissolved in water, and the mixture is kneaded, dried and granulated. Thereto are added magnesium stearate and light anhydrous silicic acid, and the mixture is compressed to give tablet cores having the active ingredient weighing 5 mg content (alternatively indicated as the weight of 70 mg each tablet). Then, said tablet cores are coated to form film-coated tablets by a conventional method, using hydroxypropylmethylcellulose, macrogol, titanium oxide, talc and light anhydrous silicic acid.

| Preparation 3: 1 % Powders: | |
|---|---|
| 3-(5-Methyl-1,2,4-oxadiazol-3-yl)-5-(3-methoxyphenyl)-1,6-naphthyridin-2(1H)-one | 5 g |
| Corn starch | 150 g |
| Lactose | 250 g |
| Hydroxypropylcellulose | 20 g |
| Light anhydrous silicic acid | 75 g |

In a conventional manner, above components are blended, granulated and regulated using a high-shear granulator, and then thereto is added light anhydrous silicic acid to give 1% powders.

INDUSTRIAL APPLICABILITY

As explained above, the compounds of the formula (I) show remarked potent retardation or inhibition of neurodegeneration due to the hypofunction of glutamic acid receptor and also exhibit low toxicity, and hence, it can be used for the prevention and/or treatment of neurodegenerative diseases such as Alzheimer's disease or schizophrenia in mammals (including human beings) as a medicine for the prevention and treatment of neurodegenerative diseases.

What is claimed is:

1. A method for treatment of schizophrenia in a mammal which comprises administering to a mammal in need of such treatment of schizophrenia an effective amount of a 5-substituted-3-oxadiazolyl-1,6-naphthyridin-2(1H)-one derivative of the following formula (I):

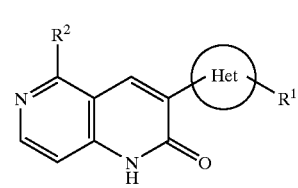

wherein:

Het is an oxadiazolyl group;

$R^1$ is a hydrogen atom, a lower alkyl group, a cyclo-lower alkyl group, a trifluoromethyl group, a lower alkenyl group, a lower alkynyl group, a lower alkoxy group, a lower alkoxy-lower alkyl group, a hydroxy-lower alkyl group, a substituted or unsubstituted aryl group, or a substituted or unsubstituted heteroaryl group; and $R^2$ is a hydrogen atom, a lower alkyl group, a cyclo-lower alkyl group, a cyclo-lower alkylmethyl group, a lower alkenyl group, a cyclo-lower alkenyl group, a lower alkynyl group, a substituted or unsubstituted aryl group, or a substituted or unsubstituted heteroaryl group, or a physiologically acceptable acid addition salt thereof.

2. The method according to claim 1, wherein the mammal is a human.

3. The method according to claim 1, wherein $R^1$ is a $C_1$ to $C_3$ alkyl group, a $C_3$ to $C_4$ cycloalkyl group, or a $C_2$ to $C_3$ alkenyl group, and $R^2$ is a hydrogen atom, a $C_1$ to $C_4$ alkyl group, a $C_3$ to $C_6$ cycloalkyl group, a substituted or unsubstituted aryl group, or a substituted or unsubstituted heteroaryl group.

4. The method according to claim 1, wherein the mammal is a human.

5. The method according to claim 1, wherein $R^1$ is a $C_1$ to $C_3$ alkyl group or $C_3$ to $C_4$ cycloalkyl group, and $R^2$ is a hydrogen atom, a $C_1$ to $C_3$ alkyl group, a $C_3$ to $C_4$ cycloalkyl group, a substituted or unsubstituted phenyl group, or a substituted or unsubstituted heteroaryl group.

6. The method according to claim 5, wherein the mammal is a human.

7. A method for treatment of schizophrenia in a mammal which comprises administering to a mammal in need of such treatment of schizophrenia an effective amount of a 5-substituted-3-oxadiazolyl-1,6-naphthyridin-2(1H)-one derivative selected from the group consisting of 3-(5-ethyl-1,2,4-oxadiazol-3-yl)-5-(2-methylcyclopropyl)-1,6-naphthyridin-2(1H)-one, 3-(5-methyl-1,2,4-oxadiazol-3-yl)-5-(2-methylphenyl)-1,6-naphthyridin-2(1H)-one, 3-(5-methyl-1,2,4-oxadiazol-3-yl)-5-(4-methoxyphenyl)-1,6-naphthyridine-2(1H)-one, 3-(5-ethyl-1,2,4-oxadiazol-3-yl)-5-(2-thienyl)-1,6-naphthyridin-2(1H)-one, 3-(5-methyl-1,2,4-oxadiazol-3-yl)-5-(4-pyridyl)-1,6-naphthyridin-2(1H)-one, 3-(3-ethyl-1,2,4-oxadiazol-5-yl)-5-methyl-1,6-naphthyridin-2(1H)-one, 3-(3-ethyl-1,2,4-oxadiazol-5-yl)-5-(3-fluorophenyl)-1,6-naphthyridin-2(1H)-one, 3-(3-methyl-1,2,4-oxadiazol-5-yl)-5-(3-methylphenyl)-1,6-naphthyridin-2(I H)-one, 3-(3-methyl-1,2,4-oxadiazol-5-yl)-5-(3-methoxyphenyl)-1,6-naphthyridin-2(1H)-one, 3-(3-ethyl-1,2,4-oxadiazol-5-yl)-5-(4-methoxyphenyl)-1,6-naphthyridin-2(1H)-one, 3-(3-ethyl-1,2,4-oxadiazol-5-yl)-5-(4-pyridyl)-1,6-naphthyridin-2(1H)-one, 3-(3-cyclopropyl-1,2,4-oxadiazol-5-yl)-5-(3-thienyl)-1,6-naphthyridin-2(1H)-one, and a physiologically acceptable acid addition salt thereof.

8. The method according to claim 7, wherein the mammal is a human.

9. A method for treatment of schizophrenia in a mammal which comprises administering to a mammal in need of such treatment of schizophrenia an effective amount of 3-(5-methyl-1,2,4-oxadiazol-3-yl)-5-(3-methoxyphenyl)-1,6-naphthyridin-2(1H)-one or a physiologically acceptable acid addition salt thereof.

10. The method according to claim 9, wherein the mammal is a human.

* * * * *

UNITED STATES PATENT AND TRADEMARK OFFICE
CERTIFICATE OF CORRECTION

PATENT NO.    : 6,743,803 B2
DATED         : June 1, 2004
INVENTOR(S)   : Kiyoshi Furukawa et al.

It is certified that error appears in the above-identified patent and that said Letters Patent is hereby corrected as shown below:

<u>Column 9,</u>
Line 26, change "claim 1" to -- claim 3 --.

Signed and Sealed this

Fifth Day of April, 2005

JON W. DUDAS
*Director of the United States Patent and Trademark Office*